United States Patent

Gurfinkel et al.

[11] Patent Number: 5,519,140
[45] Date of Patent: May 21, 1996

[54] PROCESS FOR THE MANUFACTURE OF 2-ISOPROPYL-4-METHYL-6-HYDROXYPYRIMINE

[75] Inventors: Elkana Gurfinkel, Omer; Yaacov Shmueli, Beer-Sheva, both of Israel

[73] Assignee: Makhteshim Chemical Works Ltd., Beer-Sheva, Israel

[21] Appl. No.: 457,773

[22] Filed: Jun. 1, 1995

[30] Foreign Application Priority Data

Aug. 11, 1994 [IL] Israel ......................................... 110623

[51] Int. Cl.$^6$ ................................................. C07D 239/34
[52] U.S. Cl. ................................................................ 544/319
[58] Field of Search ............................................... 544/319

[56] References Cited

U.S. PATENT DOCUMENTS 4,014,879  3/1977  Balke et al. ............................ 260/251
5,231,180  7/1993  Gurfinkel ............................... 544/243

Primary Examiner—John M. Ford
Attorney, Agent, or Firm—Browdy and Neimark

[57] ABSTRACT

Hydroxypyrimidine, a key intermediate in the manufacture of diazinon, is prepared in high yields and high purity by reacting an amidine with methyl-acetoacetate in a dry, i.e. non-aqueous, medium in the presence of a methanolic base in an aliphatic hydrocarbon solvent while azeotropically distilling off water formed during the reaction.

19 Claims, No Drawings

PROCESS FOR THE MANUFACTURE OF 2-ISOPROPYL-4-METHYL-6-HYDROXYPYRIMINE

FIELD OF THE INVENTION

The present invention concerns an improved process for preparing 2-isopropyl-4-methyl-6-hydroxypyrimidine (hereinafter "hydroxypyrimidine"), which is a key intermediate in the manufacture of diazinon, a well-known insecticide, sold in large quantities.

BACKGROUND OF THE INVENTION

Hydroxypyrimidine is generally produced in a three-stage reaction involving the formation of an imidate, amidine and the subsequent cyclization of the amidine to form the hydroxypyrimidine. Details of the prior processes used to prepare the hydroxypyrimidine are described in U.S. Pat. Nos. 4,014,879 and 5,231,180 and incorporated by their mention.

U.S. Pat. No. 4,014,879 describes a continuous ring closure process wherein the reaction is run in an aqueous sodium hydroxide solution using an excess of 20% to 30% of methyl-acetoacetate.

British Patent Number 2,083,814 runs in the reactions in a lower alkyl alcohol to cut down the excess of methyl-acetoacetate. However, yields of 90% or less were reported. Here, too, the reaction media was also water.

SUMMARY OF THE INVENTION

It is an object of the present invention to overcome deficiencies in the prior art such as indicated above. It is another object of the present invention to provide an improved method for preparing hydroxypyrimidine. It is a further objective of the present invention to provide a method more economical than known methods for the production of hydroxypyrimidine in high yields and purity.

It has been unexpectedly discovered that hydroxy-pyrimidine can be prepared by an improved method which comprises reacting an amidine of the formula

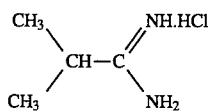

with methyl-acetoacetate, wherein the improvement consists of running the reaction in a dry, non-aqueous media. This is accomplished by running the reaction in the presence of a methanolic base in an aliphatic hydrocarbon solvent while azeotropically distilling off water during the entire reaction time.

By means of the present process commercially satisfactory reaction rates are achieved with an 8% increase in yield to 96%; in a purity of 97% with a savings of $100 to $300 per ton hydroxypyrimidine compared with the prior art process which requires a significant excess of methyl-acetoacetate. It is surmised that in the prior art methods containing water in the reaction medium, the methyl-acetoacetate and amidine react with any water present during the reaction, lowering the yields and purity.

DETAILED DESCRIPTION OF THE INVENTION

The solvent of the inventive process can be selected from one or more aliphatic hydrocarbons. Examples are hexane, heptane, octane, cyclohexane, petroleum ether 60/80, petroleum ether 80/100, petroleum ether 60/120 and a mixture of there, where heptane is the preferred solvent.

The process of the present invention enables one to use an exact molar amount of methyl-acetoacetate, which is a great saving in raw materials. However, a slight excess of up to 5 per cent, but preferably 3 per cent, may also be used.

The anhydrous methanolic base may be prepared by standard methods. The economics of the process is improved if one first optionally distills off the methanol from the remaining reaction solvent (and reuses the methanol in subsequent batches of anhydrous methanolic base), prior to the addition of the aliphatic hydrocarbon solvent. This affords cleaner methanol for recycling. Furthermore, the purity and yield of the hydroxypyrimidine is improved if one optionally adds both the methanolic base and the methyl-acetoacetate simultaneously dropwise into the reaction mixture.

The process of the present invention will also work even if the base (NaOH) is dissolved in water. However, as shown in Example 3, the yield based on the methyl-acetoacetate drops to 85% even when the methyl-acetoacetate is used in a 10% excess.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention.

EXAMPLE 1

Into a 1 liter flask with five necks (which is fitted with a mechanical stirrer, thermometer, a 20 cm reflux condenser filled with knit Mesh in front of the azeotropic set up, a dropping funnel and peristaltic pump) is added 1M of amidine hydrochloride dissolved in dry methanol and 250 ml heptane. The methanol is distilled off at up to 90° C. To the flask is added 0.5 ml FL (10%) as anti-foam. Then 122 g methyl-acetoacetate and 220 g of a 20% NaOH in methanol are simultaneously added via dip pipes while azeotropically distilling off the water and keeping the reaction at 88° C. to 90° C. At the end of this addition a further 10 g of sodium hydroxide in methanol were added. The water was distilled off over a further hour of heating until no more is distilled off. The mixture was then cooled to 70° C. and 220 ml water were added and the heptane distilled off up to a temperature of 102° C. Alternatively, water was added dropwise while the heptane was distilled off. The mixture was cooled to 20° C. acidified to a pH of 8.0 with concentrated hydrochloric acid and the solids filtered in a centrifuge. The solid cake was washed with 50 ml water at 10° C. and the hydroxypyrimidine dried in an oven for two hours at 80° C. This afforded hydroxypyrimidine in a concentration of 97%, a yield (compared with the amidine) of 96% and a yield (compared with the methyl-acetoacetate) of 93%.

EXAMPLE 2

Following a method of Example 1, a similar process was effected, except that at the beginning of the reaction only 1M of amidine hydrochloride dissolved in dry methanol was added to the flask, the methanol was distilled off at a temperature of up to 90° C., 250 ml heptane were added and the reaction run as before. This yielded hydroxypyrimidine in a concentration of 97%, a yield (based on the amidine) of 96.5% and a yield (based on the methyl-acetoacetate) of 93.5%.

EXAMPLE 3 (COMPARATIVE)

The method of Example 1 was followed, except that a 10% excess of methyl-acetoacetate was used together with the NaOH dissolved in water. The results were lower yields: 94.5% based on the amidine and 85% based on the methyl-acetoacetate.

We claim:

1. A process for the preparation of 2-isopropyl-4-methyl-6-hydroxypyrimidine comprising the steps of reacting an amidine of the formula

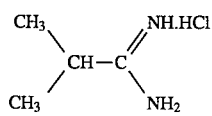

with methyl acetoacetate, the improvement consisting of running the reaction in a dry non-aqueous medium.

2. A process in accordance with claim 1 wherein the amidine is reacted with methyl-acetoacetate in an aliphatic hydrocarbon solvent while azeotropically distilling off water during the reaction.

3. A process in accordance with claim 2 wherein the aliphatic hydrocarbon solvent is selected from the group consisting of hexane, heptane, octane, cyclohexane, petroleum ether 60/80, petroleum ether 80/100, petroleum ether 60/120 and mixtures of these.

4. A process in accordance with claim 2 herein the aliphatic hydrocarbon solvent is selected from the group consisting of hexane, heptane, octane and mixtures of these.

5. A process in accordance with claim 2 wherein the aliphatic hydrocarbon solvent is heptane.

6. A process in accordance with claim 1 wherein the mole ratio of methyl-acetoacetate to amidine is 1:1 to 1:1.05.

7. A process in accordance with claim 2 wherein the mole ratio of methyl-acetoacetate to amidine is 1:1 to 1:1.03.

8. A process in accordance with claim 1 wherein both a base in methanol and methyl-acetoacetate are simultaneously added to said medium.

9. A process in accordance with claim 8 wherein the base added is dissolved in dry methanol.

10. A process for the preparation of 2-isopropyl-4-methyl-6-hydroxypyrimidine comprising the steps of reacting an amidine of the formula

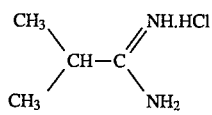

with methyl-acetoacetate in the presence of a base, the improvement consisting of running the reaction in a dry medium by running the reaction with said methyl-acetoacetate in an aliphatic hydrocarbon solvent and distilling off during the reaction water being formed.

11. A process in accordance with claim 10 wherein the aliphatic hydrocarbon solvent is selected from the group consisting of hexane, heptane, octane, cyclohexane, petroleum ether 60/80, petroleum ether 80/100, petroleum ether 60/120 and mixtures of these.

12. A process in accordance with claim 10 wherein the aliphatic hydrocarbon solvent is selected from the group consisting of hexane, heptane, octane and mixtures of these.

13. A process in accordance with claim 10 wherein the aliphatic hydrocarbon solvent is heptane.

14. A process in accordance with claim 11 wherein the mole ratio of methyl-acetoacetate to amidine is 1:1 to 1:1.05.

15. A process in accordance with claim 10 wherein the mole ratio of methyl-acetoacetate to amidine is 1:1 to 1:1.03.

16. A process in accordance with claim 10 wherein both the base and the methyl-acetoacetate are added dropwise simultaneously, and the base is a methanolic base.

17. A process in accordance with claim 10 wherein the base is dissolved in dry methanol and is added during the reaction.

18. A process for the preparation of 2-isopropyl-4-methyl-6-hydroxypyrimidine comprising the steps of reacting an amidine of the formula

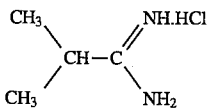

with methyl acetoacetate, the improvement consisting of running the reaction in a dry medium, and wherein the amidine is initially added in dry methanol.

19. A process according to claim 18, wherein the amidine is reacted with said methyl-acetoacetate in an aliphatic hydrocarbon solvent while azeotropically distilling off water formed during the reaction, and wherein sodium hydroxide dissolved in dry methanol is added during said reaction.

* * * * *